United States Patent [19]

Jang et al.

[11] Patent Number: 5,290,958
[45] Date of Patent: Mar. 1, 1994

[54] PHASE TRANSFER CATALYTIC PROCESS FOR PREPARING INTERMEDIATES OF ATENOLOL, PROPRANOLOL, AND THEIR DERIVATIVES

[75] Inventors: Shyue-Ming Jang; Tian-Shy Shieh, both of Hsinchu, Taiwan

[73] Assignee: Industrial Technology Research Institute, Hsinchu, Taiwan

[21] Appl. No.: 33,047

[22] Filed: Aug. 18, 1993

[51] Int. Cl.$^5$ .................. C07D 301/28; C07D 303/23; C07C 41/03; C07C 43/205
[52] U.S. Cl. ..................................... 549/517; 568/649
[58] Field of Search .......................... 549/517; 568/649

[56] References Cited

U.S. PATENT DOCUMENTS

| | | | |
|---|---|---|---|
| 2,943,096 | 6/1960 | Reinking | 549/517 |
| 3,836,671 | 9/1974 | Barrett | 424/324 |
| 4,373,073 | 2/1983 | Wojtech et al. | 549/517 |
| 4,810,808 | 3/1989 | Tomita et al. | 549/517 |
| 4,876,371 | 10/1989 | Ito et al. | 549/517 |
| 5,130,482 | 7/1992 | Takehira et al. | 549/517 |

*Primary Examiner*—Joseph E. Evans

[57] ABSTRACT

A phase transfer catalytic process for the preparation of epoxide and halohydrin intermediates, which can be subsequently and directly reacted with isopropylamine to produce beta-adrenergic antagonists such as atenolol, propanolol and their derivatives. In the process disclosed in the present invention, quaternary ammonium salts of high alkyl groups or tertiary ammonium salts of lower alkyl groups are used as catalyst in the phase transfer catalytic oxygenated-alkylation reaction between an aromatic alcohol such as p-hydroxyphenyl acetamide (for the production of atenolol) or $\alpha$-naphthol (for the production of propranolol) and epichlorohydrin to yield epoxide and halohydrin intermediates. The quaternary ammonium salts of high alkyl groups are represented by the following formula:

$$R_1-\underset{\underset{R_4}{|}}{\overset{\overset{R_3}{|}}{N}}-R_2X$$

wherein $R_1$, $R_2$, $R_3$, and $R_4$ are $C_1$ to $C_{20}$ alkyl groups and at least one of the $R_1$, $R_2$, $R_3$, or $R_4$ is a $C_9$ to $C_{20}$ alkyl group, and X is a halide group. And the tertiary ammonium salts of lower alkyl groups are presented by the following formula:

$$R_5-\underset{\underset{R_5}{|}}{\overset{\overset{R_5}{|}}{N}}-HX$$

wherein $R_5$ is a $C_1$ to $C_{20}$ alkyl group, H is hydrogen, and X is a halide group.

4 Claims, No Drawings

PHASE TRANSFER CATALYTIC PROCESS FOR PREPARING INTERMEDIATES OF ATENOLOL, PROPRANOLOL, AND THEIR DERIVATIVES

FIELD OF THE INVENTION

This invention relates to a process for preparing intermediates in the synthesis of beta-adrenergic antagonists such as atenolol, propranolol, and their derivatives. More particularly, the present invention relates to a catalytic process for the preparation of epoxide and halohydrin intermediates in the synthesis of beta-adrenergic antagonists such as atenolol, propranolol and their derivatives.

BACKGROUND OF THE INVENTION

Beta-adrenergic antagonists, or commonly referred to as beta-blockers, are important in the management of angina pectoris, hypertension and arrhythmia. The primary function of beta-blockers is to reduce the frequency of anginal episodes and raise the anginal threshold by attenuating the chronotropic and inotropic responses to adrenergic stimulation, thus diminishing myocardial oxygen consumption.

Atenolol and propranolol are two of the most commonly used beta-blockers. Atenolol is a cardioselective beta-blocker; whereas, propranolol is a nonselective beta-blocker. U.S. Pat. No. 3,836,671, issued to Barrett, et al. and assigned to Imperial Chemical Industries, discloses alkanolamine derivatives for producing beta-adrenergic blockade, and the method of producing therefor. The process disclosed therein used piperidine, which is a strong base, as a catalyst; it involved a relatively slow reaction rate (six hours to complete the reaction) and produced relatively large amounts of impurities.

In Japan Pat. Pub. 01-102,072 ('072 publication) filed by Nippon Kaya Ku (published Apr. 19, 1989), it is disclosed a process using quaternary ammonium salt of lower alkyl groups as a phase transfer catalyst during the oxygenated-alkylation step. The process disclosed in the '072 publication requires a step in which potassium hydroxide dissolved in methanol must be added as a base catalyst to convert halohydrin into epoxide before proceeding with the synthesis of the final product. Another disadvantages of this process is that methanol is known to react with epoxide to effect a nucleophilic displacement reaction thus resulting in undesirable impurities including ethers in the reaction products.

SUMMARY OF THE PRESENT INVENTION

The primary object of the present invention is to develop an improved process in the synthesis of beta-adrenergic antagonists such as atenolol, propranolol, and their derivatives. More particularly, the primary object of the present invention is to develop an improved catalytic process for the preparation of epoxide and halohydrin intermediates, which can be subsequently and directly reacted to produce beta-adrenergic antagonists such as atenolol, propranolol and their derivatives.

In the process disclosed in the present invention, quaternary ammonium salts of high alkyl groups or tertiary ammonium salts of lower alkyl groups are used as catalyst in the phase transfer catalytic oxygenated-alkylation reaction between an aromatic alcohol such as p-hydroxyphenyl acetamide (for the production of atenolol) or α-naphthol (for the production of propranolol) and epichlorohydrin to yield epoxide and halohydrin intermediates. The quaternary ammonium salts of high alkyl groups are represented by the following formula:

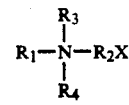

Wherein $R_1$, $R_2$, $R_3$, and $R_4$ are $C_1$ to $C_{20}$ alkyl groups and least one of the $R_1$, $R_2$, $R_3$, or $R_4$ is a $C_9$ to $C_{20}$ alkyl group, and X is a halide group.

And the tertiary ammonium salts of lower alkyl groups are presented by the following formula:

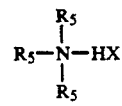

Wherein $R_5$ is a $C_1$ to $C_{20}$ alkyl group, H is hydrogen atom, and X is a halide group.

It is preferred that $R_1$, $R_2$, $R_3$, and $R_4$ are $C_1$ to $C_{16}$ alkyl groups, at least one of the $R_1$, $R_2$, $R_3$, or $R_4$ is a $C_9$ to $C_{16}$ alkyl group, and at least one of the $R_1$, $R_2$, $R_3$, or $R_4$ is a $C_1$ to $C_4$ alkyl group. It is also preferred that $R_5$ is a $C_1$ to $C_4$ alkyl group.

The reaction path employed in the present invention in the synthesis of atenolol and propranolol is described below:

Step 1: Oxygenated alkylation to make intermediates:

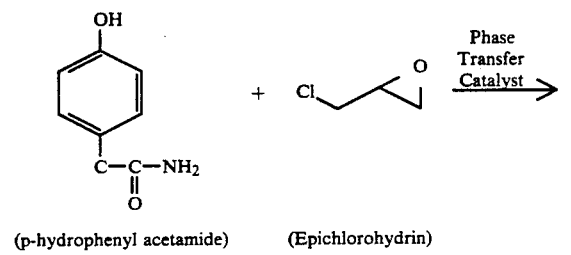

(p-hydrophenyl acetamide)   (Epichlorohydrin)

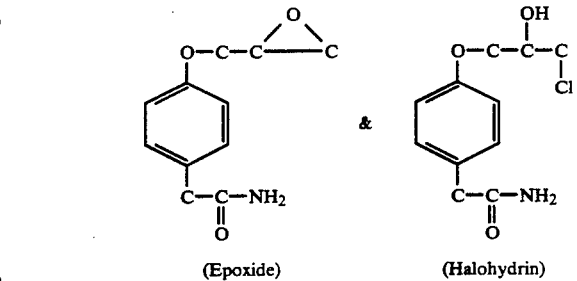

(Epoxide)   (Halohydrin)

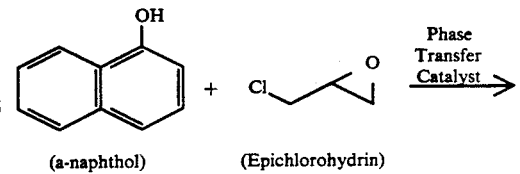

(α-naphthol)   (Epichlorohydrin)

-continued

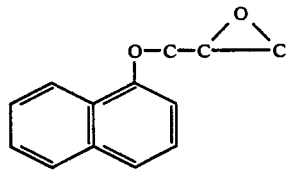

(Epoxide)

&

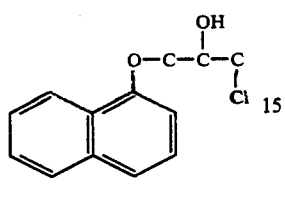

(Halohydrin)

Step 2: Nitrogenated Alkylation
(From Intermediates to Atenolol and Propranolol):

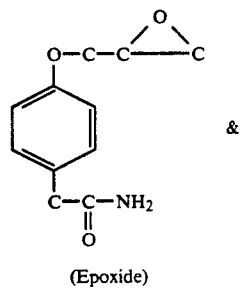

(Epoxide)

&

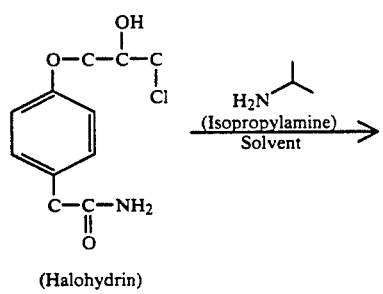

(Halohydrin)

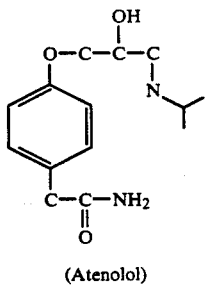

(Atenolol)

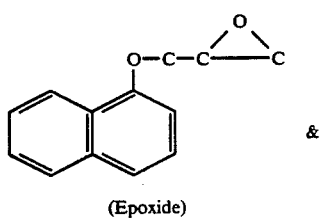

(Epoxide)

&

-continued

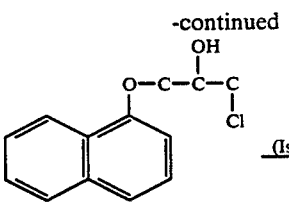

(Halohydrin)

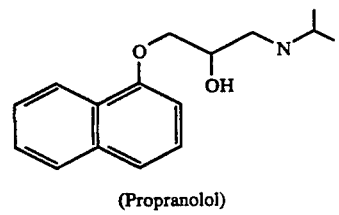

(Propranolol)

The method disclosed in the present invention uses quaternary ammonium salts of higher alkyl groups or tertiary ammonium salts of lower alkyl groups as a phase transfer catalyst; it does not require the use of strong base catalyst such as piperidine or potassium hydroxide disclosed in the prior art. With the method disclosed in the present invention, the halohydrin and epoxide intermediates can directly react with isopropyl amine in a nitrogenated-alkylation to yield atenolol, propranolol, and/or their derivatives without the step of converting halohydrin into epoxide. The present invention has several advantages over those in the prior art including faster reaction time, excellent reaction yield, no ether impurities, simplified manufacturing process, and can be more easily implemented in an industrial production process.

DETAILED DESCRIPTION OF PREFERRED EMBODIMENTS

The present invention will now be described more specifically with reference to the following examples. It is to be noted that the following descriptions of examples including preferred embodiments of this invention are presented herein for purpose of illustration and description; it is not intended to be exhaustive or to limit the invention to the precise form disclosed.

EXAMPLE 1

Example 1 describes a preferred embodiment of the present invention in the preparation of epoxide and halohydrin intermediates in the synthesis of atenolol. A reaction mixture containing 10 g of p-hydroxyphenyl acetamide, 50 ml of epichlorohydrin (i.e., 1-chloro-2,3-epoxypropane), and 0.5 g of methyltridecyl ammonium chloride was prepared. The methyltridecyl ammonium chloride, a quaternary ammonium salt of higher alkyl group, was added as a phase transfer catalyst. The reaction mixture was heated to a temperature of 90° C. and maintained there for three hours. The reaction product from such an oxygenated-alkylation was analyzed using HPLC. The yield was calculated to be 94.8%, with an epoxide to halohydrin ratio of about 3:1. The final reaction mixture was then cooled and 50 ml of water was added thereto. After filtration and drying, the final product contained 10.86 g of epoxide and halohydrin intermediates.

EXAMPLE 2

Example 2 describes the preparation of atenolol from the epoxide and halohydrin intermediates obtained from Example 1. A reaction mixture containing the epoxide and halohydrin intermediates (10.86 g) obtained from Example 1, 100 ml water, and 150 ml isopropylamine was prepared, heated to a temperature of 40° C., and maintained there for two hours. After the completion of the reaction, the reaction product was analyzed using HPLC and a yield of 90.5% was calculated. After the reaction mixture was cooled to room temperature, it was dried up to obtain a concentrated product. Then 30 ml of 2N HCl was added. The reaction mixture was filtered, and the pH of the filtrate was adjusted to 11.5 using a 30% NaOH solution. After the crystals were separated from the reaction mixture, they were filtered and dried. The final product was 10.9 g of atenolol, representing a total yield of 62% (based on p-hydroxyphenyl acetamide).

EXAMPLE 3

Example 3 describes another preferred embodiment of the present invention in the preparation of epoxide and halohydrin intermediates in the synthesis of atenolol. A reaction mixture containing 18 g of p-hydroxyphenyl acetamide, 108 ml of epichlorohydrin, and 0.9 g of trimethyl ammonium chloride, a tertiary ammonium salt of lower alkyl group, was prepared. The trimethyl ammonium chloride was added as a phase transfer catalyst. The reaction mixture was heated to a temperature of 100° C. and maintained there for one hour. The reaction product was analyzed using HPLC. The yield was calculated to be 90.5%, with an epoxide to halohydrin ratio of about 5:1. The final reaction mixture was then cooled and 60 ml of water was added thereto. After filtration and drying, the final product contained 19.62 g of epoxide and halohydrin intermediates.

EXAMPLE 4

Example 4 describes the preparation of atenolol from the epoxide and halohydrin intermediates obtained from Example 3. A reaction mixture containing the epoxide and halohydrin intermediates (19.62 g) obtained from Example 3, 96 ml water, and 190 ml isopropylamine was prepared, heated to a temperature of 55° C., and maintained there for 80 minutes. After the completion of the reaction, the reaction product was analyzed using HPLC and a yield of 94.3% was calculated. After the reaction mixture was cooled to room temperature, it was dried up to obtain a concentrated product. Then 20 ml of 6N HCl was added. The reaction mixture was filtered, and the pH of the filtrate was adjusted to 10 using a 30% NaOH solution. After the crystals were separated from the reaction mixture, they were filtered and dried. The final product was 20.61 g of atenolol, representing a total yield of 65% (based on p-hydroxyphenyl acetamide).

EXAMPLE 5

Example 5 describes yet another preferred embodiment of the present invention in the preparation of epoxide and halohydrin intermediates in the synthesis of atenolol. A reaction mixture containing 16 g of p-hydroxyphenyl acetamide, 80 ml of epichlorohydrin, and 0.96 g of tributyl ammonium bromide, a tertiary ammonium salt of lower alkyl group, was prepared. The tributyl ammonium bromide was added as a phase transfer catalyst. The reaction mixture was heated to a temperature of 105° C. and maintained there for one hour. The reaction product was analyzed using HPLC. And the yield was calculated to be 94.5%, with an epoxide to halohydrin ratio of about 4:1. The final reaction mixture was then cooled and 70 ml of water was added thereto. After filtration and drying, the final product contained 19.35 g of epoxide and halohydrin intermediates.

EXAMPLE 6

Example 6 describes the preparation of atenolol from the epoxide and halohydrin intermediates obtained from Example 5. A reaction mixture containing the epoxide and halohydrin intermediates (19.35 g) obtained from Example 5, 86 ml water, and 192 ml isopropylamine was prepared, heated to a temperature of 50° C., and maintained there for 1.5 hours. After the completion of the reaction, the reaction product was analyzed using HPLC and a yield of 93.3% was calculated. After the reaction mixture was cooled to room temperature, it was dried up to obtain a concentrated product. Then 12 ml of 6N Hcl was added. The reaction mixture was filtered, and the pH of the filtrate was adjusted to 10 using a 30% NaOH solution. After the crystals were separated from the reaction mixture, they were filtered and dried. The final product was 19.89 g of atenolol, representing a total yield of 71% (based on p-hydroxyphenyl acetamide).

EXAMPLE 7

Example 7 describes a preferred embodiment of the present invention in the preparation of epoxide and halohydrin intermediates in the synthesis of propranolol. A reaction mixture containing 30 g of α-naphthol, 30 ml of epichlorohydrin, and 0.6 g of dimethylethyl hexadecyl ammonium bromide, a quaternary ammonium salt of a higher alkyl group, was prepared. The dimethylethyl hexadecyl ammonium bromide was added as a phase transfer catalyst. The reaction mixture was heated to a temperature of 140° C. and maintained there for one hour. The reaction product was analyzed using HPLC. And the yield was calculated to be 98%, with an epoxide to halohydrin ratio of about 1:2. The final reaction mixture was then cooled and dried to concentrate the final product. The final product contained 54 g of epoxide and halohydrin intermediates.

EXAMPLE 8

Example 8 describes the preparation of propranolol from the epoxide and halohydrin intermediates obtained from Example 7. A reaction mixture containing the epoxide and halohydrin intermediates (54 g) obtained from Example 7, 120 ml water, and 120 ml isopropylamine was prepared which was heated to a temperature of 77° C. and maintained there for 6 hours under reflux. After the completion of the reaction, the reaction product was analyzed using HPLC and a yield of 93% was calculated. After the reaction mixture was cooled to room temperature, unreacted isopropylamine was removed from the reaction mixture via evaporation at reduced pressure, followed by extraction using 120 ml of dichloromethane. The temperature of the dichloromethane was reduced to $-10°$ C. to effect crystallization.

After the crystals were separated from the reaction mixture, they were filtered and dried. The final product was 20.47 g of propranolol. To recover additional propranolol, the filtrate was concentrated to a volume of 30 ml via evaporation and then cooled to a temperature of −10° C. Additional crystals were separated from the filtrate and weighed at 15.41 g. The total recovery of propranolol based on α-naphthol was calculated to be 66%.

EXAMPLE 9

Example 9 describes another preferred embodiment of the present invention in the preparation of epoxide and halohydrin intermediates in the synthesis of propranolol. A reaction mixture containing 30 g of α-naphthol, 24 ml of epichlorohydrin, and 0.6 g of ethyltripentyl ammonium iodide, a quaternary ammonium salt of a higher alkyl group, was prepared. The ethyltripentyl ammonium iodide was added as a phase transfer catalyst. The reaction mixture was heated to a temperature of 130° C. and maintained there for one hour. The reaction product was analyzed using HPLC. And the yield was calculated to be 96.3%, with an epoxide to halohydrin ratio of about 1:2. The final reaction mixture was then cooled and dried to concentrate the final product. The final product contained 49 g of epoxide and halohydrin intermediates.

EXAMPLE 10

In Example 10 propranolol was prepared from the epoxide and halohydrin intermediates obtained from Example 9, with a procedure similar to that described in Example 8. At the completion of the reaction; the reaction product was analyzed using HPLC and a yield of 94.3% was calculated. The total recovery of propranolol, based on α-naphthol, was calculated to be 61%.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are with the scope of the present invention as determined by the appended claims when interpreted in accordance with the breadth to which they are fairly, legally, and equitably entitled.

What is claimed is:

1. A method for the preparation of intermediates in the synthesis of beta-adrenergic antagonists such as atenolol, propranolol, and their derivatives, said method comprises the steps of:
   (a) preparing a reaction mixture containing:
      (i) an aromatic alcohol;
      (ii) epichlorohydrin; and
      (iii) a phase transfer catalyst which is a tertiary ammonium salt of lower alkyl groups represented by the following formula:

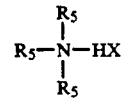

wherein $R_5$ is a $C_1$ to $C_{20}$ alkyl group, H is hydrogen, and X is a halide group; and
   (b) effectuating an oxygenated alkylation of said reaction mixture to produce epoxide and halohydrin intermediates, which can be further reacted to produce said beta-adrenergic antagonists such as atenolol, propranolol and their derivatives.

2. The method for preparing said epoxide-type and halohydrin-type intermediates according to claim 1 wherein said beta-adrenergic antagonist is atenolol and said phase transition catalyst is trimethyl ammonium chloride.

3. The method for preparing said epoxide-type and halohydrin-type intermediates according to claim 1 wherein said beta-adrenergic antagonist is atenolol and said phase transition catalyst is tributyl ammonium bromide.

4. The method for preparing said epoxide-type and halohydrin-type intermediates according to claim 1 wherein $R_5$ is a $C_1$ to $C_4$ alkyl group.

* * * * *